US00PP11729P2

(12) United States Plant Patent
Ben-Zur

(10) Patent No.: US PP11,729 P2
(45) Date of Patent: Jan. 2, 2001

(54) SPATHIPHYLLUM PLANT NAMED 'NURIT'

(75) Inventor: Issachar Ben-Zur, Tirat Yehuda (IL)

(73) Assignee: Milestone Agriculture, Inc., Apopka, FL (US)

( * ) Notice: Under 35 U.S.C. 154(b), the term of this patent shall be extended for 0 days.

(21) Appl. No.: 09/292,195

(22) Filed: Apr. 15, 1999

(51) Int. Cl.[7] ..... A01H 5/00

(52) U.S. Cl. ..... Plt./364

(58) Field of Search ..... Plt./364

(56) References Cited

U.S. PATENT DOCUMENTS

P.P. 10,627 * 9/1998 DeClercq ..... Plt./364

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Spathiphyllum plant named 'Nurit', characterized by its very compact plant habit; moderate vigor; dark green, shiny leaves that are held horizontal to the petiole; dense and bushy appearance; white spathes that are positioned above the foliage on strong and erect peduncles; long-lasting spathes; and resistance to pathogens common to Spathiphyllum.

2 Drawing Sheets

BACKGROUND OF THE INVENTION

The present invention relates to a new and distinct cultivar of Spathiphyllum plant, botanically known as Spathiphyllum hybrid, and hereinafter referred to by the cultivar name 'Nurit'.

The new cultivar is a naturally-occurring whole plant mutation of the Spathiphyllum hybrid cultivar Petite, not patented. The new Spathiphyllum was discovered by the Inventor in a controlled environment in Tirat Yehuda, Israel, in March, 1997.

The new Spathiphyllum can be compared to plants of the parent, the cultivar 'Petite'. In side-by-side comparisions conducted by the Inventor in Tirat Yehuda, Israel, plants of the new Spathiphyllum differ from plants of the cultivar 'Petite' in the following characteristics:

1. Plants of the new Spathiphyllum are more compact than plants of the cultivar 'Petite'.
2. Plants of the new Spathiphyllum have darker green, shinier, larger and more rounded leaves than plants of the cultivar 'Petite'.
3. Plants of the new Spathiphyllum are more freely clumping than plants of the cultivar 'Petite'.

Asexual propagation of the new cultivar by tissue culture in Tirat Yehuda, Israel, has shown that the unique features of this new Spathiphyllum plant are stable and reproduced true to type in successive generations of asexual propagation.

SUMMARY OF THE INVENTION

The new Spathiphyllum has not been observed under all possible environmental conditions. The phenotype may vary somewhat with variations in environment such as temperature, light intensity, and propagation procedures, without, however, any variance in genotype.

The following observations, measurements and comparisons describe five-month old plants (from microcuttings) grown in Apopka, Fla., under commercial greenhouse conditions in 10-cm containers. Day temperatures ranged from 16 to 27° C. and night temperatures ranged from 10 to 16°

C. Light was reduced by shading to 25 percent of ambient level.

The following traits have been repeatedly observed and are determined to be the unique characteristics of 'Nurit'. These characteristics in combination distinguish 'Nurit' as a new and distinct cultivar:

1. very compact plant habit.
2. Moderately vigorous.
3. Dark green, shiny leaves that are held horizontal to the petiole.
4. Very freely clumping, dense and bushy plants.
5. White spathes that are positioned above the foliage on strong and erect peduncles.
6. 1 Long-lasting spathes.
7 Resistant to pathogens common to Spathiphyllum.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical plant of 'Nurit' in a 10-cm container.

The photograph on the second sheet comprises a close-up view of typical inflorescences of 'Nurit'. Leaf, spathe and spadix colors may appear different from the actual colors due to light reflection.

DETAILED BOTANICAL DESCRIPTION

In the following description, color references are made to The Royal Horticultural Society Colour Chart except where general terms of ordinary dictionary significance are used.

Botanical classification: Spathiphyllum hybrid cultivar 'Nurit'.

Parentage Naturally-occurring whole plant mutation of Spathiphyllum hybrid cultivar 'Petite', not patented.

Propagation:

*Type.*—By tissue culture; very high multiplication rates.

*Root description.*—Freely branching, numerous thick and fleshy roots.

Plant description:

*Plant shape.*—Upright, inverted triangle, symmetrical.

*Growth habit.*—Erect when young, becoming outwardly arching as leaves develop. Freely clumping with numerous new shoots give plants a full and bushy appearance. Very compact, appropriate for 10-cm containers.

*Plant height.*—About 15 cm from soil level to top of leaf plane; about 30.5 cm from soil level to apex of spathes.

*Plant diameter.*—About 22 cm.

*Plant vigor.*—Moderately vigorous.

*Crop time.*—About five months are required to produce a finished flowering plant in 10-cm container from a tissue-cultured microcutting.

*Foliage description.*—Shape: Narrowly ovate to lanceolate. Length: About 13.5 cm. Width: About 4.75 cm. Margin: Entire, somewhat undulating. Surface: Flat, rugose. Apex: Acuminate. Base: Obtuse to cuneate. Aspect: Mature leaves held mostly perpendicular to petiole, with further development, leaves begin to reflex. Texture: Leathery, smooth, glabrous, very durable; both surfaces glossy. Color: Young, upper surface: Greener than 147A, glossy. Young, lower surface: 147B. Mature, upper surface: 147A or darker, glossy. Mature, lower surface: Darker than 147B. Venation: Upper surface: 147A, sunken. Lower surface: Close to 144A; prominent. Petiole length, primary shoots: About 11.75 cm. Petiole diameter, primary shoots, just below geniculum: About 3 mm. Geniculum diameter, primary shoots: About 3.1 mm. Petiole wing, primary shoots: Apparent on lower 75 percent of mature leaf petiole. Petiole color (including wing): Young: 144A. Fully developed: Darker than 146A and greener than 147A.

Inflorescence description:

*Inflorescence arrangement.*—Concave spathes with spadices held about 6 cm above the foliage. Inflorescences arise from leaf axils.

*Inflorescence longevity.*—Inflorescences are long-lasting, generally maintaining white color for about two or three months on the plant depending on light and temperature levels.

*Spathe.*—Shape: Oblong. Length: About 9.5 cm. Width: About 4.75 cm. Aspect: Concave, curling over the spadix. Apex: Acute. Base: Obtuse. Color, both surfaces: Before unrolling: White, 155A. Open spathe: White, 155D, with green, 146A, midvein; eventually turning green with age starting with the apex.

*Spadix.*—Length: About 3 cm. Diameter: About 1.2 cm. Color: Yellowish white to white, 155D, becoming green with age. Pollen: White, 155A; scarce to moderate amount.

*Reproductive organs.*—Typical of the species.

*Peduncle.*—Aspect: Strong and erect. Length: About 21 cm. Diameter: About 4 mm. Color: Darker than 146A and greener than 147A.

Disease resistance: Plants of the new Spathiphyllum have exhibited good resistance to pathogens common to Spathiphyllum.

Seed development: Seed development has not been observed.

It is claimed:

1. A new and distinct cultivar of Spathiphyllum plant named 'Nurit', as illustrated and described.

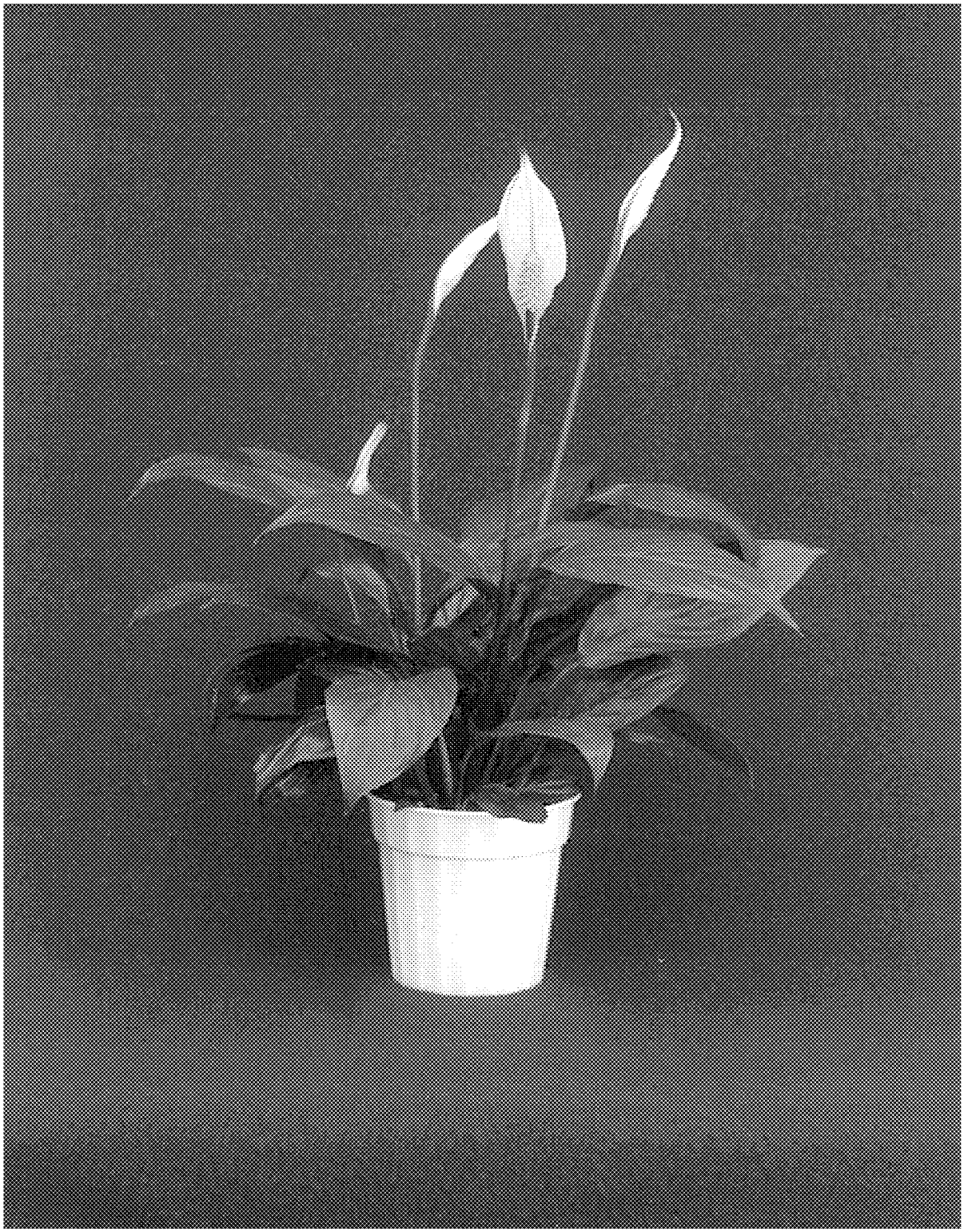

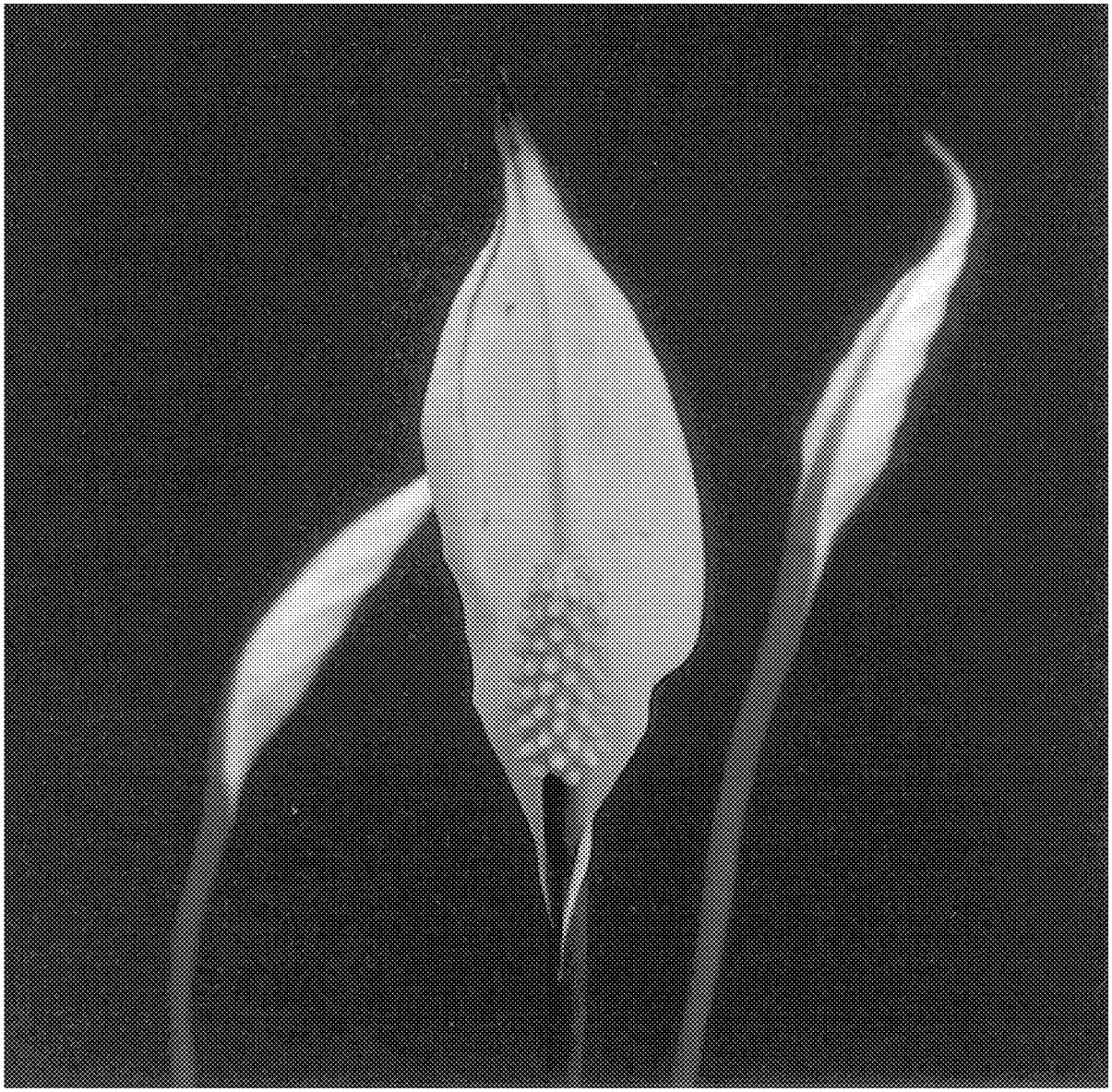

* * * * *